United States Patent
Lazzari et al.

(10) Patent No.: US 8,329,187 B2
(45) Date of Patent: Dec. 11, 2012

(54) COMPOSITIONS OF SPORES OF NON PATHOGENIC BACTERIA

(75) Inventors: Paolo Lazzari, Pula (IT); Paolo Fadda, Cagliari (IT); Luca Pani, Cagliari (IT)

(73) Assignee: Neuroscienze Pharmaness S.C. A.R.L., Pula (IT)

( * ) Notice: Subject to any disclaimer, the term of this patent is extended or adjusted under 35 U.S.C. 154(b) by 283 days.

(21) Appl. No.: 12/712,647

(22) Filed: Feb. 25, 2010

(65) Prior Publication Data

US 2010/0215745 A1    Aug. 26, 2010

(30) Foreign Application Priority Data

Feb. 25, 2009    (IT) .............................. MI2009A0264

(51) Int. Cl.
A61K 39/00    (2006.01)
A61K 39/02    (2006.01)
A61K 39/07    (2006.01)
A61K 39/08    (2006.01)

(52) U.S. Cl. ............... 424/184.1; 424/234.1; 424/246.1; 424/247.1

(58) Field of Classification Search .................. None
See application file for complete search history.

(56) References Cited

U.S. PATENT DOCUMENTS

2004/0241772 A1    12/2004    Prato
2009/0011081 A1    1/2009     Lin et al.

FOREIGN PATENT DOCUMENTS

| EP | 1405641 | A2 | 4/2004 |
| EP | 1602658 | A1 | 12/2005 |
| FR | 2889057 | A1 | 2/2007 |
| GB | 1061894 | A  | 3/1967 |
| GB | 1255284 | A  | 12/1971 |
| WO | WO-03/011341 | A1 | 2/2003 |

OTHER PUBLICATIONS

R.K. Mitra, Physico-chemical investigations of microemulsification of eucalyptus oil and water using mixed surfactants (AOT+Brij-35) and butanol, J. Collois and Interface Science, 283 (2005) 565-577.

C.E. McNamee et al., In "Physicochemical Characterization of PEG1500-12-acyloxy-stearate Micelles and Liquid Crystalline Phases", Langmuir, 2005, 21, 8146-8154.

Primary Examiner — Albert Navarro
(74) Attorney, Agent, or Firm — Arent Fox LLP

(57) ABSTRACT

Liquid-based phamaceutical and/or veterinary and/or nutraceutical compositions comprising non pathogenic sporogenic bacteria, component SP), and the following components:

O) from 0.001 to 95% by weight of one or more oils selected from esters of $C_4$-$C_{32}$ acids, $C_4$-$C_{32}$, S) from 0 to 90% by weight of one or more amphiphilic compounds, selected from surfactants, polymers forming organized structures such as aggregates, micelles, liquid crystals, vesicles, in the liquid in which they are solubilized, AD) from 0 to 60% by weight of one or more additive compounds selected from modifiers of the water and/or oil polarity, modifiers of the film curvature of component S), co-surfactants, PA) from 0.001 to 70% of one or more compounds selected from food supplements and pharmaceutical and/or veterinary active principles, W) from 0.1 to 99.9% by weight of water or saline aqueous solution, optionally buffered, the sum of the percentages by weight of the components, excluding SP), is 100%.

29 Claims, No Drawings

COMPOSITIONS OF SPORES OF NON PATHOGENIC BACTERIA

The present invention relates to liquid based compositions comprising an aqueous phase, an oil phase and of non pathogenic bacteria spores.

More specifically the present invention refers to liquid-based compositions for pharmaceutical, veterinary or nutraceutic use comprising an aqueous phase, an oil phase and bacterial spores of the *Bacillus* genus, such as *Bacillus subtills* and *Bacillus clausii*.

The use of bacterial spores of the *Bacillus* genus for pharmaceutical use is known, in particular for the treatment and the prevention of diseases and disorders correlated to an unbalance of the intestinal flora, this treatment having also a beneficial effect on the immune system.

GB 1,061,894 discloses therapeutic preparations containing spores of non pathogenic bacteria of the *Bacillus* genus, such as *Bacillus Clostridium* and *Bacillus bifidus*, glutamic acid or its alkaline metal salts, and at least one substance capable to buffer the preparation at pH values comprised between 4.0 and 9.0.

Patent application EP 1,405,641 describes the combination of spores of *Bacillus subtilis* and/or *Bacillus clausii* with non sporogenic probiotic microorganisms, such as lacto-bacilli, for pharmaceutical and/or nutraceutical use.

Said spore-containing formulations are generally administered in association with other preparations containing food supplements for treating diseases and disorders correlated to an unbalance of the intestinal flora.

Liquid pharmaceutical compositions containing bacterial spores of the *Bacillus* genus used for the treatment and prevention of intestinal dismicrobisms, endogenous disvitaminosis, unbalances of the intestinal bacterial flora, in particular following diarrhoea conditions and/or antibiotics or chemotherapeutics administration, are commercialized in vials with the commercial names Enterogermina® or Enterum®. These pharmaceutical compositions contain only water and *Bacillus clausii* spores (strain number I-273, I-274, I-275, I-276, deposited according to the Budapest treaty c/o CNCM Istituto Pasteur). The pharmaceutical compositions contain 2 milliards of spores in 5 ml of water commercial product.

The drawback of these liquid pharmaceutical compositions is that the spore number is rather limited.

Another drawback is that in these aqueous pharmaceutical compositions other active principles that could be added must be soluble in water.

Patent application WO 03/011,341 describes solid pharmaceutical preparations of spores of non pathogenic bacteria of *Bacillus* genus, such as *Bacillus subtilis* and *Bacillus clausii*. In particular the pharmaceutical preparations of the above mentioned patent application are formed of bacterial spores of the *Bacillus* genus adsorbed on a solid water-insolubile matrix, for example kaolin, and of a cellulose derivative, for example methylcellulose or microcrystalline cellulose. These solid pharmaceutical preparations, in the form of capsules or tablets, allow to formulate a high number of spores, allowing concentrations of spores, referred to one gram of the final composition, comprised between 3 and 30 milliards. This solid pharmaceutical preparation of non pathogenic bacterial spores of the *Bacillus* genus can be administered also as a dispersion in water or in another suitable liquid.

The solid compositions described in this patent application make available, as said, formulations having a number of spores higher than those of liquid compositions. However the disadvantage is that the solid compositions are not fully accepted by all the users, as they are difficult to be swallowed.

As said, the therapeutic or prophylactic use of the above described pharmaceutical and/or veterinary and/or nutraceutical preparations containing spores of non pathogenic bacteria generally requires the combination of these preparations with food supplements, for example vitamins and mineral salts, and/or with pharmaceutical active principles, for example those having antidiarrhoeic activity. The drawback is that said pharmaceutical active principles and supplements are generally insoluble in the aqueous liquid spore-containing formulations.

In general for oral use liquid pharmaceutical formulations, both fluid or viscous, are preferred by the users to the solid ones, for example tablets or capsules, as more easily swallowable.

The need was felt to have available single liquid-based pharmaceutical formulations, comprising spores of non pathogenic bacteria and food supplements, for example vitamins and/or mineral salts, and/or pharmaceutical and/or veterinary active principles, for the prophylaxis or therapy of diseases and/or disorders in human beings and/or in mammals. More in particular, the need was felt to have available single liquid based pharmaceutical formulations comprising spores of non pathogenic bacteria of the *Bacillus* genus, preferably polyantibiotic-resistant, such as *Bacillus subtilis* and *Bacillus clausii*, food supplements and/or pharmaceutical and/or veterinary active principles, for the prophylaxis or therapy of diseases and/or disorders of the gastrointestinal tract and of the immune system in human beings and in mammals.

Pharmaceutical and/or veterinary and/or nutraceutical compositions solving the above described technical problem have been surprisingly and unexpectedly found by the Applicant.

An object of the present invention is liquid based phamaceutical and/or veterinary and/or nutraceutical compositions comprising a component SP), comprising one or more non pathogenic sporogenic bacteria including the non pathogenic bacteria of the *Bacillus* genus *Bacillus subtilis* and *Bacillus clausii*, and the following components (% by weight) acceptable for pharmaceutical and/or veterinary and/or nutraceutical use:

O) 0.001 to 95%,
S) 0 to 90% of one or more amphiphilic compounds, selected from the following classes:
    surfactants, selected from non-ionic, anionic, cationic and amphoteric surfactants, optionally containing fluorine atoms,
    polymers forming organized structures such as aggregates, micelles, liquid crystals, vesicles, in the liquid in which they are solubilized,
AD) 0 to 60% of one or more additive compounds selected from the following classes:
    modifiers of the water and/or oil polarity,
    modifiers of the curvature of the film of component S),
    co-surfactants,
PA) 0.001 to 70% of one or more compounds selected from food supplements and pharmaceutical and/or veterinary active principles, respectively for nutraceutical, pharmaceutical and/or veterinary compositions,
W) 0.1 to 99.9% by weight of water or saline aqueous solution, optionally buffered,
the sum of the percentages by weight of the components of composition A) is 100% excluding component SP),
wherein
    when component SP) is *Bacillus clausii*, component O) is one or more oils selected from the following classes of compounds;

esters of $C_4$-$C_{32}$ acids having a linear or branched chain, optionally containing one or more unsaturations, preferably of ethylene type, $C_4$-$C_{32}$ acids having a linear or branched chain, optionally containing one or more unsaturations, preferably of ethylene type, which are included into the liquid composition when the pH is comprised between 3 and 5, when component SP) is a non pathogenic sporogenic bacterium different from *Bacillus clausii* component O) is one or more oils selected from the following:

esters of $C_4$-$C_{12}$ and $C_{16}$ saturated acids having a linear or branched chain, $C_4$-$C_{32}$ saturated acids having a linear or branched chain which are included into the liquid composition, when the pH is comprised between 3 and 5, in this case preferably the compositions do not include edible milk, soymilk and thereof fermentation products.

A further object of the invention are liquid based pharmaceutical and/or veterinary and/or nutraceutic compositions comprising component SP) comprising non pathogenic sporogenic bacteria, including the non pathogenic bacteria of the *Bacillus* genus *Bacillus subtilis* and *Bacillus clausii*, and the composition (A') comprising (% by weight) the following components acceptable for pharmaceutical and/or veterinary and/or nutraceutical use:

O) 0.001 to 95,

S) 0 to 90% of one or more amphiphilic compounds, selected from the following classes:

surfactants, selected from non-ionic, anionic, cationic and amphoteric surfactants, optionally containing fluorine atoms, polymers forming organized structures such as aggregates, micelles, liquid crystals, vesicles, in the liquid in which they are solubilized, AD) 0 to 60% of one or more additive compounds selected from the following classes:

modifiers of the water and/or oil polarity, modifiers of the curvature of the film of component S), co-surfactants, W) 0.1 to 99.9% by weight of water or saline aqueous solution, optionally buffered, the sum of the percentages by weight of the components, excluding component SP), is 100% excluding component SP), in the composition component PA) is zero, i.e. it is not present, wherein when component SP) is *Bacillus clausii*, component O) is one or more oils selected from the following classes of compounds:

esters of $C_{4-C32}$ acids having a linear or branched chain, optionally containing one or more unsaturations, preferably of ethylene type, $C_4$-$C_{32}$ acids having a linear or branched chain, optionally containing one or more unsaturations, preferably of ethylene type, which are included into the liquid composition when the pH is comprised between 3 and 5, when component SP) is a non pathogenic sporogenic bacterium different from *Bacillus clausii*, component O) is one or more oils selected from the following:

esters of $C_4$-$C_{12}$ and $C_{16}$ saturated acids having a linear or branched chain, $C_4$-$C_{32}$ saturated acids having a linear or branched chain which are included into the liquid composition, when the pH is comprised between 3 and 5, in this case preferably the compositions do not include edible milk, soymilk and thereof fermentation products.

Preferably component SP) is present in the compositions of the invention at concentrations comprised between 0.01 and 30 milliards/g of the total weight of the composition, more preferably between 0.02 and 15 milliards/g of the total weight of the composition. More preferably component SP) is *Bacillus* genus, still more preferably component SP) is a polyantibiotic resistant *Bacillus*, in particular *Bacillus subtilis*, preferably *Bacillus clausii* (strain number I-273, I-274, I-275, I-276, deposited according to Budapest treaty c/o CNCM Istituto Pasteur).

Further examples of component SP) are *Bacillus coagulans, Bacillus licheniformis, Escherichia coli* strain nissle, *Propionibacterium freudenreichii*, and their mixtures.

The liquid compositions of the present invention can contain an amount of spores for gram of composition even higher than the corresponding of the liquid formulations that are available on the market.

Optionally component W) is buffered at pHs comprised between 3 and 9, more preferably between 4 and 8.

The liquid based compositions of the invention can be both fluid and viscous. The latter are optionally formed of gels and/or liquid crystals in one of the known forms, for example lamellar, cubic, hexagonal forms.

Preferably component PA) is selected from the following classes; vitamins, mineral salts, antioxidant compounds, natural extracts, pharmaceutical or veterinary active principles. The pharmaceutical of veterinary active principles are preferably selected from those used for the prophylaxis or therapy of diseases and/or disorders of the gastrointestinal tract or of the immune system.

Edible milk generally comes from cows, but also from other mammals such as goats, sheep, water buffalo, yaks or horses.

A fermentation products of edible milk are for instance yogurth.

Preferably, also in the case wherein the non pathogenic sporogenic bacterium is *Bacillus clausii*, edible milk, soya milk and thereof fermentation products are excluded from the compositions of the present invention.

Optionally to the compositions of the invention component NSP) can be added non sporogenic probiotic microorganisms, or mixtures thereof, such as lactobacilli (for example of the acidophilus type), streptococci (for example *Streptococcus thermophilus*), bifidi (for example *Bifidobacterium bifidum*). Examples of these microorganisms are reported in EP 1,405,641.

Component NSF), when present, is at concentrations from 0.01 to 30 milliards/g of the composition (excluding component NSP)).

Optionally in the formulations of the invention components SP) and/or NSP) can be adsorbed on particles of a water-insoluble matrix acceptable for veterinary and/or pharmaceutical and/or nutraceutical use.

The water-insoluble matrix is formed for example by clays, kaolins, calcium carbonate, colloidal silica, magnesium and aluminum silicate, cellulose derivatives and bentonite derivatives. Among the cellulose derivatives the following compounds can for example be mentioned: microcrystalline cellulose, methylcellulose, hydroxypropyl-methylcellulose. Preferably the water-insoluble matrix is formed of a mixture of kaolin and a cellulose derivative, preferably microcrystalline cellulose.

The ratio by weight component SP) and/or NSP)/water-insoluble matrix is preferably in the range 90/10-10/90, more preferably 70/30-30/70, still more preferably 60/40-40/60, the ratio 50/50 is particularly preferred.

The particles have a high specific surface area. In particular the particles have a size such that 90% of the number of particles have an average diameter lower than or equal to 130 micrometers. Preferably 60% of the number of particles have an average diameter lower than or equal to 60 micrometers.

Inert lubricants, such as stearic acid salts, for example magnesium stearate, other inert additives such as gelatin and titanium dioxide, can be to the formulations of the invention, having the components SP) and/or NSP) adsorbed on a water-insoluble matrix.

By the term adsorbed it is meant that the component and/or NSP) is bound to the water-insoluble matrix with any type of bond, for example a chemical, physical, biological bond, etc. The bond must be labile to allow the release of component SP) in the gastrointestinal tract, preferably in the digestive tract.

Preferably in the compositions of the present invention component S) is comprised between 0.001 and 80%, more preferably between 0.01 and 50% (% by w).

Components O) and W) in the composition of the invention can form two distinct phases or, they can be partially or totally mixed with each other, preferably when component S) is present and optionally also component AD). Said mixtures comprising W) O), S) and optional AD) are in the form of microemulsions, emulsions, liquid crystals or gels.

By microemulsions it is meant a system formed of two or more phases immiscible with each other, the system being transparent, isotropic and it comprises at least an aqueous phase and at least an oil phase, the various phases being stabilized by component S), optionally in the presence of one or more components AD). See as a reference R. K. Mitra, Physicochemical investigations of microemulsification of eucalyptus oil and water using mixed surfactants (AOT+Brij-35) and butanol, J. Colloid and Interface. Science, 283 (2005) 565-577.

By emulsion it is meant a system formed of the same components of the microemulsions but having an opalescent or milky appearance, or having the form and consistency of cream.

The emulsions and the microemulsions can be water/oil, oil/water, bicontinuous or multiple. Examples of the latter are for instance the oil/water/oil or water/oil/water emulsions or microemulsions.

The microemulsions of the present invention are stable in a wide range of temperature, generally from 0° C. to 80° C., preferably from 4° C. to 45° C.

The microemulsions of the present invention can be prepared with a process comprising the following steps:
(IP) optionally, solubilization of the component PA) in component O), obtaining an oily solution of component PA)
(IIP) addition of component S) to component O), or to the corresponding oily solution obtained in (IP), obtaining an oily phase comprising components S) and optionally PA)
(IIIP) optionally, addition of component AD) to the oily phase obtained in (IIP), obtaining an oily phase comprising components AD), S), and optionally PA),
(IVP) addition, under stirring, of water or of a saline aqueous solution to the oily phase obtained in (IIP) or in the optional step (IIIP), obtaining a limpid solution that is the microemulsion.

The steps of the process can be carried out at temperatures in the range 0° C.-80° C.

It is possible to obtain a microemulsion in the form of a limpid solution also by varying the order of performance of the above mentioned steps, or, for example, by proceeding as follows;
(IP') optionally solubilization of the component PA) incomponent O), obtaining an oily solution of component PA),
(IIP') addition of component S) to water or to a saline aqueous solution, obtaining an aqueous phase comprising components S),
(IIIP') optionally, addition of component AD) to the aqueous phase, obtaining an aqueous phase comprising components S) and AD)
(IVP') mixing under stirring of component O) or of the oily solution of step (IP') with the aqueous phase of step (IIP') or optionally step (IIIP'), obtaining the microemulsion.

The temperature range at which one operates is the same as indicated above.

The emulsions of the present invention can be prepared by a process comprising the following steps:
(IP'') optionally, solubilization of the component PA) in component O), optionally in the presence of component AD),
(IIP'') heating of component O), or of the oily solution obtained in the optional step (IP'') at temperatures in the range 35° C.-80° C., more preferably 45-70° C.,
(IIIP'') addition of component S) to water or to a saline aqueous solution, optionally including component AD),
(IVP'') heating of the aqueous phase of step (IIIP'') at temperatures in the range 35° C.-80° C., more preferably 45-70° C.
(VP'') addition, under stirring of the oily phase obtained in step (IIP'') to the aqueous phase obtained in step (IVP''), obtaining an emulsion,
(VIP'') cooling of the emulsion at temperatures comprised between 0° C. and 30° C.

Step (VP'') preferably is performed by using turboemulsifiers.

The liquid phases (emulsions) obtained in steps (VP'') and (IVP'') can optionally be subjected to a further homogeneization step at high pressure.

The emulsions can also be prepared by dilution of microemulsions with water or with aqueous solutions or with component O). Component AD) can be included in each of the following liquid phase; water, the aqueous solution and component O).

By liquid crystal or liquid-crystalline phase it is meant a phase formed of component S) and of component O) or of component W), or mixtures thereof, optionally in the presence of component AD), wherein component S) is in an organized structure imparting to the liquid phase a high viscosity. Liquid-crystalline phases of high viscosity comprising components S) such as lamellar, hexagonal, cubic, liquid-crystalline phases, are known in the prior art.

The preferred compositions are those wherein the spores of component SP), as such or adsorbed on the water-insoluble matrix, are dispersed in a microemulsion or in liquid crystals. These compositions are much requested from an industrial point of view as they are stable. In fact, also in case of phase separation it is always possible to restore the composition for example by simple stirring.

Another object of the present invention are the pharmaceutical formulations comprising the compositions of the present invention.

The pharmaceutical formulations of the present invention can be made so that they are ready-to-use with the components thereof kept in separate compartments and mixed with each other at the time when the formulation is to be used.

In this case the pharmaceutical formulation can for example be formed of component SP) dispersed in component W), the dispersion kept separated from component O). In this case the two phases are admixed at the time of use.

Alternatively, the pharmaceutical formulation can for example be formed of component SP), optionally adsorbed on a water-insoluble matrix, kept separated from both component W) and component O). Component SP) is dispersed in component W) and in component O) at the time of use.

Another pharmaceutical formulation can for example be formed of component SP) dispersed in a portion of component W), the dispersion kept separated from component O) and also from the remaining portion of component W). the dispersion of component SP) is mixed with the remaining portion of component W) and with component O) at the time of use.

The pharmaceutical formulation for example, can be also in the form of a pharmaceutical dispenser, wherein component SP) is separated from components O) and W). At the time of use components SP), O) and W) are mixed with each other. For instance, in a pharmaceutical dispenser component SP) can be stored in a compartment attached to the dispenser cap.

In another embodiment Component SP) is dispersed in a part of the totality of component W) and the dispersion is kept separated from the other component. The same when component SP) is adsorbed on a water-insoluble matrix.

In the above mentioned pharmaceutical formulations wherein compound SP) is kept in a separated compartment, components W) and O) can be kept together, optionally with components S) and optionally AD) in one compartment, or each of said components is in a separate compartment, or components W) and O) can be kept in separated compartments and the components mixed at the time of use.

As said, the two components W) and O) mixed with each other can form, in the presence of component S) and optionally component AD), microemulsions, emulsions, or liquid crystals.

The above described pharmaceutical formulations, which allow to prepare the ready-to-use compositions of the invention can comprise also component PA) and/or component NSP) and/or, whether not present already, component S) and/or component AD).

It is a further object of the present invention a dispenser for the pharmaceutical formulations for preparing the ready-to-use compositions of the present invention.

In component S) the surfactants containing fluorine atoms can have (per)fluorinated chains, for example (per)fluoropolyether chains.

The liquids in which the polymers of component S) are solubilized to form the organized structures are water and/or oil. The oils that can be used are mentioned hereinafter and can be of both natural and synthetic origin.

The preferred surfactants component S) are the non-ionic and anionic ones. Among the non-ionic surfactants, the most preferred are those containing polyoxyalkylene chains, preferably polyoxyethylene chains. The following ones can for example be mentioned:

polyoxyl 35 castor oil, commercially known for example with the trademark Cremophor® EL (BASF), manufactured by ethoxylation of castor oil, polyoxyl 40 hydrogenated castor oil, commercially known for example with the trademark Cremophor® RH40 (BASF), manufactured by ethoxylation of hydrogenated castor oil, polyethylenglycol 15 hydroxystearate, commercially known for example with the trademark Solutol® HS15 (BASF), prepared by reaction of 15 moles of ethylene oxide with 1 mole of 12-hydroxystearic acid, polyoxyethylene polysorbate, such as Tween® 80, Tween® 20, Tween® 60, Tween® 85, sorbitan esters of fatty acids, as sorbitan monolaurate and sorbitan monostearate, commercialized for example with the trademark Span® 20 and Span® 60, respectively, vitamin E/TPGS: tocopheryl propylenglycol 1000 succinate, polyoxyethylen ethers of fatty acids, as those of the series Brij®, as Brij® 35, Brij® 76, Brij® 98, PEG-12-acyloxy-stearates, see for example C. E. McNamee et al. in "Physicochemical Characterization of PEG 1500-12-acyloxy-stearate micelles and liquid crystalline phases", Langmuir, 2005, 21, 8146-8154, among these the following can for example be mentioned:

PEG 1500 mono-12-capryloyloxy stearate (PEG 1500-$C_{18}C_8$)

PEG 1500 mono-12-caproyloxy stearate (PEG 1500-$C_{18}C_{10}$)

PEG 1500 mono-12-lauroyloxy stearate (PEG 1500-$C_{16}C_{12}$)

PEG 1500 mono-12-myristoyloxy stearate (PEG 1500-$C_{18}C_{14}$)

PEG 1500 mono-12-palmitoyloxy stearate (PEG 1500-$C_{18}C_{16}$).

Among the anionic surfactants the following can for example be mentioned: soya lecithin, for example commercially known with the trademark Epikuron® 200, bis-2-ethylhexylsulphosuccinate (AOT), sodium taurocholate.

Among cationic surfactants, hexadecyltrimethylammonium bromide (CTAB) and didodecylammonium bromide (DDAB) can for example be mentioned.

The polymers which can be used as component S) must be soluble in the aqueous phase and/or in the oily phase of the pharmaceutical composition of the present invention. By the term soluble it is meant that the polymers must reach in the phase in which they are soluble concentrations at least equal to those at which organized structures as aggregates, micelles, liquid crystals, vesicles, are formed. The presence of said organized structures can be checked by specific techniques of the physical chemistry of the dispersed systems, as for example Laser Light Scattering (LLS), Neutron Scattering, microscopy.

As said, the polymers component S) can also be used in combination with the above reported surfactants. Also in this case the concentration of the polymer solubilized in the liquid phase used must be such to lead to the formation of the above said organized structures.

The polymers component S) are for example polyvinylpyrrolidone and vinylpyrrolidone/vinyl acetate copolymers, commercialized for example with the trademark Kollidon®, as Kollidon® 12PF and Kollidon® 17PF (BASF), and the block copolymers containing polyoxyalkylene chains, more preferably containing polyoxyethylene chains (PEO), as for example the block copolymers FED with polyoxypropylene chains (PPO) characterized by PEO-PPO-PEO structures, commercially available for example with the trademark Pluronic® or Poloxamer® or Lutrol®, as Lutrol® F68 and Lutrol® F127 commercialized by Basf.

In component O) the acid esters are preferably obtained by esterification of the corresponding acid, preferably an aliphatic carboxylic acid, with an alcohol having an aliphatic chain, preferably $C_1$-$C_5$, or having a polyoxyethylene chain, or with glycerine. In the latter case mono-, di- or triglycerides are obtained.

The following esters can for example be mentioned:
oleoyl macrogol 6 glyceride (unsaturated polyglycosylated glyceride), commercialized for example with the trademark Labrafil® 1944 CS, (Gattefossé),
propylenglycol caprylate caprate, commercially known for example with the trademark Labrafac® PG (Gattefossé),
propylenglycol monoester of the caprylic acid, commercialized for example with the trademark Capmul® PG-8 (Abitec),
glycerol oleate (for example Peceol® (Gattefossé)),
medium chain mono- and diglycerides, for example capric and caprylic acid glycerides (for example Capmul® MCM (Abitec), Imwitor® 308 (Sasol)),
polyglycerol oleate (for example Pluro® oleic (Gattefossé)),
capric/caprylic acid triglycerides (for example Miglyol® 812 and Miglyol® 810 (Sasol), Labrafac® CC CS (Gattefossé)),
ethyl butyrate, ethyl caprylate, ethyl oleate, tripalmitine, commercialized for example with the trademark DYNASAN® 116 by Sasol.

Vegetable oils having a pharmaceutical degree purity, containing one or more of the above mentioned esters can also be used. The soya oil can for example be mentioned.

Among the acids component O) the preferred ones are the aliphatic carboxylic acids and in particular the fatty acids. The following acids can be mentioned: stearic acid, omega 3 acids and omega-6 acids.

In component AD) the modifiers of the water and/or oil polarity can be for example polyethylenglycols. Lutrol®E300 and Lutrol®E400 (BASF) can be mentioned. Aliphatic alcohols, for example ethanol, can also be used.

When component AD) is a modifier of the film curvature of component S), component AD) is selected for example from aliphatic alcohols, preferably $C_2$-$C_5$.

In component AD) the co-surfactants can be for example surfactant compounds as defined above, or aliphatic alcohols, preferably having a chain with at least 6 carbon atoms. There can be mentioned for example:
propylen glycol monolaurate, commercially known for example with the trademark Capmul® PG12 (Gattefossé) or Lauroglycol® 90 (Gattefossé),
caprylocaproyl macrogol 8 glyceride (saturated ethyldiglycosylated glyceride) commercialized for example with the trademarks Labrasol®, Gelucire 44-14 (Gattefossé),
diethylenglycol monoethyl ether, commercially known for example with the trademark Transcutol® (Gattefossé).

The vitamins of component PA) are those known in the prior art. The vitamins of the groups A, B, C, D, E, K, M, P, PP can be for example mentioned. Carotenoids can for example be mentioned in vitamin A group, riboflavin in vitamin B group, ascorbic acid in vitamin C group, tocopherol in vitamin D group, biotin in vitamin H group, folic acid in vitamin M group, bioflavonoids in vitamin P group.

The mineral salts of component PA) are the saline integrators such as citrates and gluconates, for example potassium citrate, sodium citrate, zinc gluconate, manganese gluconate, iron gluconate. Other saline integrators that can be used are for example alkaline metal salts, such as potassium phosphate and sodium chloride.

The antioxidants of component PA) are natural or synthetic antioxidants having an antioxidant action or proantioxidant which slow down or prevent the oxidation of other compounds. Vitamins, carotenoids, polyphenols, minerals, glutathione, enzymes such as catalase and superoxide dismutase can be for example mentioned as antioxidants. Among these, the vitamins of groups A, B, C, E, carotenoids, flavonoids, antocyanidines, flavanols, tannins, lycopene, coenzyme Q10, zinc, selenium, germanium, resveratrol can be in particular mentioned.

The specific active principles PA) for use in the prophylaxis and treatment of diseases and/or disorders of the gastrointestinal tract are for example intestinal antimicrobics, such as the antibiotics nistatin, streptomycin, amphotericin; opioids such as loperamide, intestinal antiinflammatories such as corticosteroids and antiallergenic substances such as the chromoglycic acid.

The natural extracts of component PA) are whole or refined extracts obtained from officinal plants. In particular the natural extracts having constipating and/or coadjuvant properties are preferred in the treatment of pathologies and disorders of the gastrointestinal tract.

The compositions of the invention can also contain conventional natural and/or synthetic additives, or mixtures thereof.

The additives must be suitable for the above mentioned uses and are selected for example from glutamic acid and alkaline metal salts thereof, dyestuffs, preservatives, aromatizers, etc.

it is a further object of the present invention the use of the compositions of the invention as a medicament and in particular for the treatment of the above mentioned diseases and disorders.

It is a further object of the present invention the use of the compositions of the invention for preparing drugs for the prophylaxis and therapy of diseases and disorders in mammals and in human beings.

Preferably the use of the compositions of the present invention concerns the prophylaxis and therapy of diseases and disorders in mammals and in human beings of the gastrointestinal tract and of the immune system.

The diseases and disorders of the gastrointestinal tract which can be treated with the pharmaceutical compositions of the present invention are for example intestinal inflammations, disorders related to the mineral salt deficiency, intestinal dismicrobism, endogenous vitamin deficiency, unbalances of the intestinal bacterial flora, in particular caused by diarrhoea conditions and/or following administration of antibiotics or chemotherapeutics.

The compositions of the invention can also be used, for blocking the Helycobacter pilori action when associated with specific antibiotics, The use of the compositions of the present invention for preparing drugs for the treatment of the various pathologies can be performed by using the known methods used for said treatments.

In particular the administration of the compositions of the invention must be performed so that the amount of active principle is effective for the specific treatment. The dosages, the administration routes and the posologies are determined depending on the disease typology, on the pathology severity, on the physical conditions and characteristics of the patient, such as age, weight, response to the active principle, on the pharmacokinetics and toxicology of the active principle for the specific treatment.

The preferred daily dosage of component SP) is from 1 to 10 milliards of spores/day, preferably from 2 to 8 milliards.

The present invention relates furthermore to the compositions of the invention for preparing drugs for the prophylaxis and therapy of diseases and disorders in mammals and, in human beings. Preferably the present invention relates to pharmaceutical compositions for preparing drugs for the prophylaxis and therapy of the diseases and disorders of the gastrointestinal tract and of the immune system in mammals and in human beings.

A further object of the present invention is represented by nutraceutical products comprising the compositions of the present invention and their use as coadjuvants in the prophylaxis and in the treatment of the above mentioned pathologies and disorders. They can be used with the pharmaceutical compositions of the present invention or with the drugs of the prior art used for the above treatments The following examples are reported for a better understanding of the present invention but are not meant to be limitative of the scope of the invention.

EXAMPLES

Example 1

Preparation of a Composition of the Invention Containing a Dispersion in Microemulsion of Spores of *Bacillus Clausii* Adsorbed on Kaolin 5 grams of a microemulsion were prepared by mixing the following compounds: commercial triglyceride Miglyol® 810N (0.20 g), commercial monoglyceride Imwitor® 308 (0.20 g), nonionic surfactant Solutol® HS15 (0.85 g) and a physiological solution (3.75 g).

To said microemulsion 0.56 g of the pooled content of two commercial capsules of Enterogermina®, formed of 4 milliards of spores of *Bacillus Clausii* (I-273, I-274, I-275, I-276) adsorbed on kaolin in the presence of microcrystalline and comprising cellulose, magnesium stearate, gelatin, titanium dioxide, were added.

A dispersion of spores of *Bacillus Clausii*, adsorbed on kaolin, in microemulsion was obtained.

The final composition thus obtained is homogeneous without phase separation up to 5 minutes from the preparation. For longer periods, it is observed that the initial aspect of the composition can be restored by stirring.

In the final composition a complete precipitation of the suspended solids takes place in a period of time of 25 minutes from the preparation.

Example 1a (Comparative)

A formulation having a similar composition but without oil is prepared. It is observed that the precipitation is completed after 3 minutes, Example 2

Preparation of a Composition of the Invention Containing a Dispersion in Microemulsion of Spores of *Bacillus Clausii* Adsorbed on Kaolin 1.25 grams of an oily solution were prepared by mixing the following components: the commercial triglyceride Miglyol® 810N (0.20 g), the commercial monoglyceride Imwitor® 308 (0.20 g), the nonionic surfactant Solutol® HS15 (0.85 g).

To said oily solution an aqueous dispersion formed of 3.75 g of distilled water and 0.56 of the pooled content of two commercial capsules of Enterogermina® corresponding to 4 milliards of spores of *Bacillus Clausii* (I-273, I-274, I-275, I-276) adsorbed on kaolin and comprising microcrystalline cellulose, magnesium stearate, gelatin, titanium dioxide, was added under stirring.

A dispersion of spores of *Bacillus Clausii*, adsorbed on kaolin, in microemulsion was obtained.

The obtained final composition is homogeneous without phase separation up to 5 minutes from the preparation. In any case it is noted that the initial aspect of the composition can be restored by stirring.

Example 3

Preparation of a Composition of the Invention Containing a Dispersion in a Liquid-crystalline Phase of Spores of *Bacillus Clausii* Adsorbed on Kaolin 4.70 grams of a lamellar liquid-crystalline phase were prepared by mixing the following components: the commercial triglyceride Miglyol® 810N (0.20 g), the non ionic surfactant Solutol® HS15 (3.25 g) and 1.25 g of distilled water.

To the liquid-crystalline phase 0.56 of the pooled content of two commercial capsules of Enterogermina® corresponding to 4 milliards of spores of *Bacillus Clausii* (I-273, I-274, I-275, I-276) adsorbed on kaolin and comprising microcrystalline cellulose, magnesium stearate, gelatin, titanium dioxide, were added.

A dispersion of spores of *Bacillus Clausii*, adsorbed on kaolin, in a lamellar liquid-crystalline phase was obtained.

The obtained final composition is highly viscous and remains homogeneous without phase separation for at least 2 hours from the preparation.

Example 4

Preparation of a Composition of the Invention Containing a Dispersion in Microemulsion of Spores of *Bacillus Clausii*

28.2 grams of an oily solution were prepared by mixing the following components: the commercial triglyceride Miglyol® 810N (5.6 g) and the nonionic surfactant Solutol® HS15 (22.6 g).

To the oily solution the content of a 5 ml commercial vial of an aqueous formulation of Enterogermina®, containing 2 milliards of spores of *Bacillus Clausii* (I-273, I-274, I-275, I-276), was added.

The obtained final composition remains limpid without phase separation for at least 20 days.

Example 5

Preparation of a Composition of the Invention Containing a Dispersion in Microemulsion of Spores of *Bacillus Clausii*

1.25 grams of an oily solution were prepared by mixing the following components the commercial triglyceride Miglyol® 810N (0.21 g) and the nonionic surfactant Solutol® HS15 (1.00 g).

To the oily solution the content of a 5 ml commercial vial of an aqueous formulation of Enterogermina®, containing 2 milliards of spores of *Bacillus Clausii* (I-273, I-274, I-275, I-276), was added.

A dispersion of spores of *Bacillus Clausii* in microemulsion was attained.

The obtained final composition results homogeneous, slightly opalescent, without phase separation for at least 2 hours from the preparation. For longer times it is observed that the initial aspect of the composition is restored by stirring.

Example 6

Preparation of a Composition of the Invention Containing a Dispersion in a Liquid-crystalline Phase of Spores of *Bacillus Clausii*

20.0 grams of an oily solution were prepared by mixing the commercial triglyceride Miglyol® 810N (4.0 g) with the nonionic surfactant Solutol® HS15 (16.0 g).

To the oily solution the content of a 5 ml commercial vial of an aqueous formulation of Enterogermina®, containing 2 milliards of spores of *Bacillus Clausii* (I-273, I-274, I-275, I-276), was added.

The obtained composition is highly viscous and is formed of a lamellar liquid crystalline phase. The composition is homogeneous, without phase separation for at least eight hours from the preparation.

Example 7

Preparation of a Composition of the Invention Containing a Dispersion in a Liquid-crystalline Phase of Spores of *Bacillus Clausii*

100.0 grams of a microemulsion were prepared by mixing the commercial triglyceride Miglyol® 810N (17.0 g), the non-ionic surfactant Solutol® HS15 (65.0 g) and distilled water (15.0 g).

95.0 grams of the microemulsion were mixed with the content of a 5 ml commercial vial of an aqueous formulation of Enterogermina® containing 2 milliards of spores of *Bacillus Clausii* (I-273, I-274, I-275, I-276).

The obtained final composition is highly viscous and is formed of a lamellar liquid-crystalline phase. The composition is homogeneous, without phase separation for at least eight hours from the preparation.

Example 8

Preparation of a Composition of the Invention Containing a Dispersion of Spores of *Bacillus Clausii*, Adsorbed on Kaolin, in a Microemulsion Containing Tocopherol Ten grams of a microemulsion were prepared by mixing the commercial triglyceride Miglyol® 810N (1.53 g), tocopherol (0.17 g), the nonionic surfactant Solutol® HS15 (6.80 g) and distilled water (1.5 g).

0.56 g of the pooled content of two commercial capsules of Enterogermina®, corresponding to 4 milliards of spores of *Bacillus Clausii* (I-273, I-274, I-275, I-276) adsorbed on kaolin and comprising microcrystalline cellulose, magnesium stearate, gelatin, titanium dioxide, were added to the microemulsion under stirring.

A dispersion of spores of *Bacillus Clausii*, adsorbed on kaolin, in a microemulsion containing the lipophilic compound tocopherol, was obtained.

The composition results homogeneous without phase separation up to 5 minutes from the preparation. The homogeneity can be restored by stirring.

Example 9

Preparation of a Composition of the Invention Containing a Dispersion of Spores of *Bacillus Clausii*, Adsorbed on Kaolin, in a MicroeEmulsion Containing Tocopherol and Mineral Salts Example 8 was repeated but using, instead of distilled water, the same weight of an aqueous solution of sodium citrate (0.1 M) and monopotassium phosphate (0.2 M).

A dispersion of spores of *Bacillus Clausii*, adsorbed on kaolin, in a microemulsion containing mineral salts (sodium citrate and monopotassium phosphate), and the lipophilic compound tocopherol, was obtained.

The obtained final composition is homogeneous without phase separation up to 5 minutes from the preparation. The homogeneity of the composition can be restored by stirring.

Example 10

Preparation of a Composition of the Invention Containing a Dispersion of Spores of *Bacillus Clausii*, Adsorbed on Kaolin in an Emulsion Containing a Cannabinoidergic Compound having a Constipating Activity An emulsion (10 g) was prepared by mixing 9.8 grams of the commercial emulsion Tocrisolve® commercialized by Tocris with 0.2 g of the water-soluble agonist cannabinoidergic compound WIN 55.212-2.

Said latter compound, as other agonist cannabinoid derivatives, is known to have a constipating activity. In fact it slackens the gastrointestinal transit, as it is shown in example 6 of EP 1,602,658.

0.56 g of the pooled content of two commercial capsules of Enterogermina®, corresponding to 4 milliards of spores of *Bacillus Clausii* (I-273, I-274, I-275, I-276) adsorbed on kaolin, comprising also microcrystalline cellulose, magnesium stearate, gelatin and titanium dioxide, were added to the emulsion under stirring.

A dispersion of spores of *Bacillus Clausii*, adsorbed on kaolin, in an emulsion containing the agonist cannabinoidergic compound WIN 55.212-2, was obtained.

The invention claimed is:
1. Liquid based pharmaceutical and/or veterinary and/or nutraceutical compositions comprising a component SP) comprising one or more non pathogenic sporogenic bacteria, and the following components (% by weight) acceptable for pharmaceutical and/or veterinary and/or nutraceutical use:
O) 0.001 to 95%,
S) 0 to 90% of one or more amphiphilic compounds, selected from the following classes:
surfactants, selected from non-ionic, anionic, cationic and amphoteric surfactants, optionally containing fluorine atoms,
polymers forming aggregates, micelles, liquid crystals, vesicles, in the liquid in which they are solubilized,
AD) 0 to 60% of one or more additive compounds selected from the following classes:
modifiers of the water and/or oil polarity,
modifiers of the curvature of the film of component S),
co-surfactants,

PA) 0.001 to 70% of one or more compounds selected from food supplements and pharmaceutical and/or veterinary active principles, respectively for nutraceutical, pharmaceutical and/or veterinary compositions, W) 0.1 to 99.9% by weight of water or saline aqueous solution, optionally buffered, the sum of the percentages by weight of the components, excluding component SP), is 100%, wherein when component SP) is *Bacillus clausii*, component O) is one or more oils selected from the following classes of compounds:

esters of $C_4$-$C_{32}$ acids having a linear or branched chain, optionally containing one or more unsaturations, $C_4$-$C_{32}$ acids having a linear or branched chain, optionally containing one or more unsaturations, which are included into the liquid composition when the pH is comprised between 3 and 5, when component SP) is a non pathogenic sporogenic bacterium different from *Bacillus clausii* component O) is one or more oils selected from the following:

esters of $C_4$-$C_{12}$ and $C_{16}$ saturated acids having a linear or branched chain, $C_4$-$C_{32}$ saturated acids having a linear or branched chain which are included into the liquid composition, when the pH is comprised between 3 and 5, in this case the compositions do not include edible milk, soymilk and thereof fermentation products.

2. Liquid-based pharmaceutical and/or veterinary and/or nutraceutic compositions component SP) comprising one or more non pathogenic sporogenic bacteria, and the following components (% by weight) acceptable for pharmaceutical and/or veterinary and/or nutraceutical use:

O) 0.001 to 95%,

S) 0 to 90% of one or more amphiphilic compounds, selected from the following classes:

surfactants, selected from non-ionic, anionic, cationic and amphoteric surfactants, optionally containing fluorine atoms, polymers forming aggregates, micelles, liquid crystals, vesicles, in the liquid in which they are solubilized, AD) 0 to 60% of one or more additive compounds selected from the following classes:

modifiers of the water and/or oil polarity, modifiers of the curvature of the film of component S), co-surfactants, W) 0.1 to 99.9% by weight of water or saline aqueous solution, optionally buffered, the sum of the percentages by weight of the components, excluding component SP), is 100%, in the composition component PA) is zero, wherein PA is a compound selected from food supplements and pharmaceutical and/or veterinary active principles, and wherein when component SP) is *Bacillus clauslii*, component O) is one or more oils selected from the following classes of compounds:

esters of $C_4$-$C_{32}$ acids having a linear or branched chain, optionally containing one or more unsaturations, $C_4$-$C_{32}$ acids having a linear or branched chain, optionally containing one or more unsaturations, which are included into the liquid composition when the pH is comprised between 3 and 5, when component SP) is a non pathogenic sporogenic bacterium different from *Bacillus clausii*, component 0) is one or more oils are selected from the following:

esters of $C_4$-$C_{12}$ and $C_{16}$ saturated acids having a linear or branched chain, $C_4$-$C_{32}$ saturated acids having a linear or branched chain which are included into the liquid composition, when the pH is comprised between 3 and 5, in this case the compositions do not include edible milk, soymilk and thereof fermentation products.

3. Compositions according to claim 1, wherein component SP) is present at concentrations comprised between 0.01 and 30 milliards/g of the total weight of the composition.

4. Compositions according to claim 1, wherein component SP) belongs to the *Bacillus* genus.

5. Compositions according to claim 1, wherein component W) is buffered at pHs comprised between 3 and 9.

6. Compositions according to claim 1, wherein component PA) is selected from the following classes: vitamins, mineral salts, antioxidant compounds, natural extracts, pharmaceutical or veterinary active principles.

7. Compositions according to claim 6, wherein the pharmaceutical or veterinary active principles are selected from those for the prophylaxis or the therapy of diseases and/or disorders of the gastrointestinal tract or of the immune system.

8. Compositions according to claim 1, further comprising non sporogenic probiotic microorganisms component NSP), or their mixtures.

9. Compositions according to claim 8, wherein components SP) and/or NSP) are adsorbed on particles of a water-insoluble matrix.

10. Compositions according to claim 9, wherein the water-insoluble matrix is formed of one or more of the following substances: clays, kaolins, calcium carbonate, colloidal silica, magnesium and aluminum silicate, cellulose derivatives or bentonite derivatives.

11. Compositions according to claim 9, wherein the water-insoluble matrix is formed of a mixture of kaolin and a cellulose derivative.

12. Compositions according to claim 9, wherein the ratio by weight component SP)/water-insoluble matrix is in the range 90/10-10/90.

13. Compositions according to claim 9, wherein 90% of the number of particles have a particle diameter lower than or equal to 130 micrometers, and 60% of the number of particles have a particle diameter lower than or equal to 60 micrometers.

14. Compositions according to claim 1, wherein components O) and W) form two distinct phases or they are partially or totally mixed when component S) and AD) are present.

15. Compositions according to claim 14, wherein the mixtures of components O) and W) in the presence of component S) and optional AD) are in the form of microemulsions, emulsions, liquid crystals or gels.

16. Compositions according to claim 1, wherein the spores of component SP), as such, or adsorbed on a water-insoluble matrix, are dispersed in a mioroemulsion or in liquid crystals.

17. Ready-to-use pharmaceutical formulations according to claim 1, wherein the components of the compositions are kept in separate compartments and are mixed with each other at the time when the ready-to-use formulation is to be used.

18. The compositions according to claim 1 formed of a dispersion of component SP) in component W), kept separated from component O).

19. The compositions according to claim 1, wherein component SP), optionally adsorbed on a water-insoluble matrix, is kept separated from both component W) and from component O).

20. The compositions according to claim 1, formed of component SP) dispersed in a portion of component W), the dispersion being separated from component O) and from the left portion of component W).

21. The compositions according to claim 19, wherein components W) and O) form two distinct phases and are kept in one compartment or each of components W) and O) are kept in a separate compartment.

22. The compositions according to claim 19, wherein components W), O) together with component S) and optionally AD), are kept in one compartment.

23. The compositions of claim 1, wherein component SP) is in the form of spores.

24. The compositions of claim 4, wherein component SP) is selected from polyantibiotic resistant *Bacillus* genus.

25. The compositions of claim 5, wherein component W) is buffered at pHs comprised between 4 and 8.

26. The compositions of claim 12, wherein the ratio by weight component SP)/water-insoluble matrix is in the range of 70/30 to 30/70.

27. The compositions of claim 12, wherein the ratio by weight component SP)/water-insoluble matrix is in the range of 60/40 to 40/60.

28. The compositions of claim 12, wherein the ratio by weight component SP)/water-insoluble matrix is 50/50.

29. The compositions of claim 1, wherein component SP) comprises bacteria selected from *Bacillus subtilis* and *Bacillus clausii*.

* * * * *